(12) United States Patent
Jennings et al.

(10) Patent No.: US 11,123,492 B2
(45) Date of Patent: Sep. 21, 2021

(54) INJECTION DEVICE

(71) Applicant: Cilag GmbH International, Zug (CH)

(72) Inventors: Douglas Ivan Jennings, Hertfordshire (GB); Ahmad Bitar, Cambridge (GB)

(73) Assignee: Cilag GmbH International, Zug (CH)

( * ) Notice: Subject to any disclaimer, the term of this patent is extended or adjusted under 35 U.S.C. 154(b) by 671 days.

(21) Appl. No.: 14/897,369

(22) PCT Filed: Jun. 11, 2014

(86) PCT No.: PCT/EP2014/062167
§ 371 (c)(1),
(2) Date: Dec. 10, 2015

(87) PCT Pub. No.: WO2014/198798
PCT Pub. Date: Dec. 18, 2014

(65) Prior Publication Data
US 2016/0129195 A1 May 12, 2016

(30) Foreign Application Priority Data
Jun. 11, 2013 (GB) .................................... 1310402

(51) Int. Cl.
*A61M 5/315* (2006.01)
*A61M 5/20* (2006.01)
(Continued)

(52) U.S. Cl.
CPC ...... *A61M 5/31501* (2013.01); *A61M 5/2033* (2013.01); *A61M 5/31586* (2013.01);
(Continued)

(58) Field of Classification Search
CPC ............ A61M 5/31501; A61M 5/3204; A61M 5/31586; A61M 5/2033; A61M 2005/208;
(Continued)

(56) References Cited

U.S. PATENT DOCUMENTS

| | | |
|---|---|---|
| 1,845,036 A | 2/1932 | Busher |
| 2,019,382 A | 10/1935 | Aronson |

(Continued)

FOREIGN PATENT DOCUMENTS

| | | |
|---|---|---|
| CA | 2445511 A1 | 11/2002 |
| CH | 518102 A | 1/1972 |

(Continued)

OTHER PUBLICATIONS

International Search Report dated Jul. 9, 2004; International Application No. PCT/GB03/05494.
(Continued)

*Primary Examiner* — Jenna Zhang
(74) *Attorney, Agent, or Firm* — Steven J. Schwarz

(57) ABSTRACT

An injection device comprises an actuator adapted when actuated to cause commencement of an injection sequence; a locking mechanism adapted to be moved between a locked position in which the locking mechanism prevents the actuator from being actuated, and an unlocked position in which the actuator can be actuated to cause commencement of the injection sequence. An indicator is configured to provide a visual indication of whether the locking mechanism is in its locked position or in its unlocked position.

17 Claims, 7 Drawing Sheets

(51) Int. Cl.
*A61M 5/32* (2006.01)
*A61M 5/24* (2006.01)
*A61M 5/31* (2006.01)

(52) U.S. Cl.
CPC ..... *A61M 5/3204* (2013.01); *A61M 2005/206* (2013.01); *A61M 2005/2006* (2013.01); *A61M 2005/208* (2013.01); *A61M 2005/2403* (2013.01); *A61M 2005/3125* (2013.01)

(58) Field of Classification Search
CPC .. A61M 2005/3125; A61M 2005/2403; A61M 2005/206; A61M 2005/2006; A61M 5/326; A61M 2005/3267; A61M 2005/3247
See application file for complete search history.

(56) References Cited

U.S. PATENT DOCUMENTS

| | | |
|---|---|---|
| 2,147,616 A | 2/1939 | Chaput |
| 2,295,849 A | 9/1942 | Kayden |
| 2,531,267 A | 11/1950 | Harisch |
| 2,752,918 A | 7/1956 | Rooseboom |
| 2,764,977 A | 10/1956 | Ferguson |
| 2,828,742 A | 4/1958 | Ashkenaz |
| 2,845,065 A | 7/1958 | Gabriel |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Ben Moura |
| 3,674,033 A | 7/1972 | Powers |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A | 12/1980 | Wickham |
| 4,299,238 A | 11/1981 | Baidwan et al. |
| 4,333,459 A | 6/1982 | Becker |
| 4,373,526 A | 2/1983 | Kling |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,500,310 A | 2/1985 | Christinger |
| 4,507,118 A | 3/1985 | Dent |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,695,274 A | 9/1987 | Fox |
| 4,717,383 A | 1/1988 | Phillips et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 4,994,034 A | 2/1991 | Botich et al. |
| 5,009,646 A | 4/1991 | Sudo et al. |
| 5,026,349 A | 6/1991 | Schmitz et al. |
| 5,057,079 A | 10/1991 | Tiemann et al. |
| 5,073,170 A | 12/1991 | Schneider |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,188,613 A | 2/1993 | Shaw |
| 5,190,526 A | 3/1993 | Murray et al. |
| 5,242,400 A | 9/1993 | Blake et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,385,551 A | 1/1995 | Shaw |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,634,906 A | 6/1997 | Foster et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |

(56) References Cited

U.S. PATENT DOCUMENTS

| | | |
|---|---|---|
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,891,086 A * | 4/1999 | Weston ............... A61M 5/30 604/70 |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,989,229 A | 11/1999 | Chiappetta |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart |
| 6,209,738 B1 | 4/2001 | Jansen et al. |
| 6,221,044 B1 | 4/2001 | Grecco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 * | 9/2001 | Safabash ............... A61M 5/158 604/136 |
| RE37,439 E | 11/2001 | Firth et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie |
| 6,391,003 B1 | 5/2002 | Lesch |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,536,723 B1 | 3/2003 | Nakatani |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,579,269 B1 | 6/2003 | Kleyman |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,155 B2 | 3/2010 | Raven et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,785,292 B2 | 8/2010 | Harrison |
| 7,794,434 B2 | 9/2010 | Mounce et al. |

(56) References Cited

U.S. PATENT DOCUMENTS

| | | | |
|---|---|---|---|
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 * | 11/2012 | Barrow-Williams | A61M 5/2033 604/134 |
| 8,317,751 B2 * | 11/2012 | Habeshaw | A61M 5/2033 604/138 |
| 8,343,110 B2 | 1/2013 | Burnell |
| 8,409,138 B2 | 4/2013 | James et al. |
| 8,409,141 B2 | 4/2013 | Johansen et al. |
| 8,491,530 B2 | 7/2013 | Maritan |
| 8,556,861 B2 | 10/2013 | Tsals |
| 8,696,628 B2 | 4/2014 | Grunhut |
| 8,932,264 B2 | 1/2015 | DeSalvo |
| 8,968,236 B2 | 3/2015 | Jennings et al. |
| 9,028,451 B2 | 5/2015 | Jennings |
| 9,248,245 B2 | 2/2016 | Ekman et al. |
| 9,314,574 B2 | 4/2016 | Roberts et al. |
| 9,358,346 B2 | 6/2016 | Beyeler |
| 9,592,350 B2 | 3/2017 | Roberts et al. |
| 9,675,757 B2 | 6/2017 | Harrison |
| 9,757,520 B2 | 9/2017 | Corrigan |
| 10,588,983 B2 | 3/2020 | Bookbinder et al. |
| 2001/0005781 A1 | 6/2001 | Bergens et al. |
| 2001/0021826 A1 | 9/2001 | Fisher et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0039394 A1 * | 11/2001 | Weston | A61M 5/30 604/72 |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078496 A1 * | 4/2003 | Price | G01F 11/023 600/431 |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0187405 A1 | 10/2003 | Gatti |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2004/0254526 A1 * | 12/2004 | Weston | A61M 5/30 604/68 |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0165360 A1 | 7/2005 | Stamp |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 * | 11/2005 | Khalaj | A61M 5/20 604/181 |
| 2005/0261634 A1 * | 11/2005 | Karlsson | A61M 5/2033 604/197 |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0129089 A1 * | 6/2006 | Stamp | A61M 5/30 604/93.01 |
| 2006/0161111 A1 | 7/2006 | Potter et al. |
| 2006/0178630 A1 | 8/2006 | Bostrom et al. |

(56) References Cited

U.S. PATENT DOCUMENTS

| | | | |
|---|---|---|---|
| 2006/0178631 A1 | 8/2006 | Gillespie et al. | |
| 2006/0178642 A1 | 8/2006 | Gillespie et al. | |
| 2006/0184119 A1 | 8/2006 | Remde et al. | |
| 2006/0184137 A1 | 8/2006 | Reynolds | |
| 2006/0189938 A1 | 8/2006 | Hommann et al. | |
| 2006/0200093 A1 | 9/2006 | Lopez | |
| 2006/0206060 A1 | 9/2006 | Lopez | |
| 2006/0224124 A1 | 10/2006 | Scherer | |
| 2006/0229572 A1 | 10/2006 | Lopez | |
| 2006/0258986 A1 | 11/2006 | Hunter et al. | |
| 2006/0258990 A1 | 11/2006 | Weber | |
| 2006/0270986 A1 | 11/2006 | Hommann et al. | |
| 2007/0021716 A1 | 1/2007 | Hansen | |
| 2007/0027430 A1 | 2/2007 | Hommann | |
| 2007/0032775 A1 | 2/2007 | Niedospial et al. | |
| 2007/0066939 A1 | 3/2007 | Krulevitch et al. | |
| 2007/0078382 A1 | 4/2007 | Hommann et al. | |
| 2007/0078428 A1 | 4/2007 | Reynolds et al. | |
| 2007/0118094 A1 | 5/2007 | Bingham et al. | |
| 2007/0135767 A1* | 6/2007 | Gillespie | A61M 5/2033 604/135 |
| 2007/0142787 A1 | 6/2007 | Scherer | |
| 2007/0150842 A1 | 6/2007 | Chaudhri et al. | |
| 2007/0156091 A1 | 7/2007 | Fathallah et al. | |
| 2007/0156112 A1 | 7/2007 | Walsh | |
| 2007/0208296 A1 | 9/2007 | Paproski et al. | |
| 2007/0244456 A1 | 10/2007 | Fangrow | |
| 2007/0244457 A1 | 10/2007 | Fangrow | |
| 2007/0244458 A1 | 10/2007 | Fangrow | |
| 2007/0244459 A1 | 10/2007 | Fangrow | |
| 2007/0244460 A1 | 10/2007 | Fangrow | |
| 2007/0244461 A1 | 10/2007 | Fangrow | |
| 2007/0244462 A1 | 10/2007 | Fangrow | |
| 2007/0244463 A1 | 10/2007 | Warren et al. | |
| 2007/0244464 A1 | 10/2007 | Fangrow et al. | |
| 2007/0244465 A1 | 10/2007 | Fangrow | |
| 2007/0244466 A1 | 10/2007 | Fangrow | |
| 2008/0033395 A1 | 2/2008 | Alchas | |
| 2008/0071225 A1 | 3/2008 | Hommann et al. | |
| 2008/0154192 A1 | 6/2008 | Schraga | |
| 2008/0161770 A1 | 7/2008 | Fangrow | |
| 2008/0172001 A1 | 7/2008 | Reynolds et al. | |
| 2008/0172024 A1 | 7/2008 | Yow | |
| 2008/0213590 A1 | 9/2008 | Greiner et al. | |
| 2008/0249462 A1 | 10/2008 | Nilufer et al. | |
| 2008/0249498 A1 | 10/2008 | Fangrow | |
| 2008/0262427 A1 | 10/2008 | Hommann | |
| 2008/0269680 A1 | 10/2008 | Ibranyan et al. | |
| 2008/0306443 A1 | 12/2008 | Neer et al. | |
| 2008/0312590 A1* | 12/2008 | Barrow-Williams | A61M 5/2033 604/134 |
| 2008/0312592 A1 | 12/2008 | Barrow-Williams et al. | |
| 2008/0312602 A1 | 12/2008 | Barrow-Williams et al. | |
| 2008/0312606 A1 | 12/2008 | Harrison et al. | |
| 2009/0036764 A1 | 2/2009 | Rivas et al. | |
| 2009/0054849 A1 | 2/2009 | Burnell et al. | |
| 2009/0088688 A1 | 4/2009 | Timothy Donald et al. | |
| 2009/0149812 A1 | 6/2009 | MacAulay | |
| 2009/0209554 A1 | 8/2009 | Boyd et al. | |
| 2009/0234297 A1 | 9/2009 | Jennings | |
| 2010/0016793 A1 | 1/2010 | Jennings et al. | |
| 2010/0036319 A1 | 2/2010 | Drake et al. | |
| 2010/0049125 A1* | 2/2010 | James | A61M 5/2033 604/110 |
| 2010/0063444 A1 | 3/2010 | Wikner | |
| 2010/0234811 A1* | 9/2010 | Schubert | A61M 5/326 604/198 |
| 2010/0286714 A1 | 11/2010 | Gyrn et al. | |
| 2010/0292653 A1 | 11/2010 | Maritan | |
| 2011/0092954 A1 | 4/2011 | Jennings | |
| 2011/0098647 A1 | 4/2011 | Jennings | |
| 2011/0098655 A1* | 4/2011 | Jennings | A61M 5/2033 604/192 |
| 2011/0098656 A1 | 4/2011 | Burnell et al. | |
| 2011/0130743 A1 | 6/2011 | Jennings et al. | |
| 2011/0144594 A1 | 6/2011 | Sund et al. | |
| 2011/0172640 A1 | 7/2011 | Cronenberg et al. | |
| 2011/0245761 A1 | 10/2011 | Dean et al. | |
| 2011/0282278 A1 | 11/2011 | Stamp et al. | |
| 2012/0046615 A1 | 2/2012 | Iwase et al. | |
| 2012/0232491 A1 | 9/2012 | Jennings | |
| 2012/0283698 A1 | 11/2012 | Millerd | |
| 2012/0323177 A1* | 12/2012 | Adams | A61M 5/2033 604/135 |
| 2013/0046246 A1* | 2/2013 | Cross | A61M 5/326 604/189 |
| 2013/0060232 A1 | 3/2013 | Adlon et al. | |
| 2013/0096512 A1 | 4/2013 | Ekman et al. | |
| 2013/0125441 A1 | 5/2013 | Westwood et al. | |
| 2013/0150801 A1 | 6/2013 | Barrow-Williams et al. | |
| 2013/0267898 A1 | 10/2013 | Hourmand et al. | |
| 2013/0310759 A1 | 11/2013 | Barrow-Williams et al. | |
| 2013/0317446 A1 | 11/2013 | Hourmand et al. | |
| 2013/0331794 A1 | 12/2013 | Ekman et al. | |
| 2013/0338601 A1* | 12/2013 | Cowe | A61M 5/2033 604/189 |
| 2013/0345643 A1 | 12/2013 | Hourmand et al. | |
| 2014/0207106 A1* | 7/2014 | Bechmann | A61M 5/326 604/506 |
| 2014/0221974 A1 | 8/2014 | Bechmann et al. | |
| 2014/0257185 A1 | 9/2014 | Bechmann et al. | |
| 2014/0257193 A1 | 9/2014 | Bostrom et al. | |
| 2015/0025458 A1 | 1/2015 | Heald et al. | |
| 2015/0051551 A1* | 2/2015 | Hirschel | A61M 5/31585 604/189 |
| 2015/0190590 A1 | 7/2015 | Macarthur et al. | |
| 2018/0312590 A1 | 11/2018 | Cogswell et al. | |

FOREIGN PATENT DOCUMENTS

| | | |
|---|---|---|
| CH | 703993 | 3/2012 |
| CN | 2059579 U | 7/1990 |
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 387465 | 1/1924 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 2/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 11/2003 |
| EP | 0096314 A2 | 12/1983 |
| EP | 0144625 A2 | 6/1985 |
| EP | 0240787 A2 | 10/1987 |
| EP | 0338806 A2 | 10/1989 |
| EP | 0515473 B1 | 12/1992 |
| EP | 0518416 A1 | 12/1992 |
| EP | 0331452 B1 | 8/1993 |
| EP | 0585626 A1 | 3/1994 |
| EP | 0389938 B1 | 5/1994 |
| EP | 0516473 B1 | 2/1996 |
| EP | 0111724 B1 | 2/1998 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |

(56) References Cited

FOREIGN PATENT DOCUMENTS

| | | |
|---|---|---|
| EP | 1124601 B1 | 12/2004 |
| EP | 1364667 B1 | 4/2005 |
| EP | 1208858 B1 | 6/2006 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 1755710 B1 | 3/2012 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2319560 | 5/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2268342 | 9/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 A | 5/1920 |
| GB | 412054 A | 6/1934 |
| GB | 728248 A | 4/1955 |
| GB | 909898 A | 11/1962 |
| GB | 1263355 A | 2/1972 |
| GB | 1311937 A | 3/1973 |
| GB | 1514725 A | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 30-001091 | 1/1930 |
| JP | 49-77487 | 7/1974 |
| JP | 49-021036 | 6/1979 |
| JP | 54-087694 | 1/1982 |
| JP | 59-115053 A | 7/1984 |
| JP | 2-185261 A | 7/1990 |
| JP | 2-502971 T | 9/1990 |
| JP | H 02-299660 A | 12/1990 |
| JP | 03-129156 | 12/1991 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-065786 | 3/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-154005 | 5/2003 |
| JP | 2003-284776 | 10/2003 |
| JP | 2003-532500 T | 11/2003 |
| JP | 2003-533288 A | 11/2003 |
| JP | 2004-033737 A | 2/2004 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2005-534433 | 11/2005 |
| JP | 2006-223858 A | 8/2006 |
| JP | 2007-207611 A | 8/2007 |
| JP | 2008-284177 A | 11/2008 |
| JP | 2008-295590 | 12/2008 |
| JP | 2008-543500 | 12/2008 |
| JP | 2012-503995 | 2/2012 |
| JP | 2013-529527 | 7/2013 |
| KR | 10-2008-0004473 | 1/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 A1 | 11/1988 |
| WO | WO 1988/10129 A1 | 12/1988 |
| WO | WO 92/19296 A | 11/1992 |
| WO | WO 1993/02186 A1 | 2/1993 |
| WO | WO 93/21986 A2 | 11/1993 |
| WO | WO 1993/23098 A1 | 11/1993 |
| WO | WO 1994/04207 A1 | 3/1994 |
| WO | WO 94/07554 A1 | 4/1994 |
| WO | WO 94/11041 A1 | 5/1994 |
| WO | WO 94/13342 A1 | 6/1994 |
| WO | WO 94/013343 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/31235 A1 | 11/1995 |
| WO | WO 1995/29720 A1 | 11/1995 |
| WO | WO 1995/35126 A1 | 11/1995 |
| WO | WO 95/35126 A1 | 12/1995 |

(56) References Cited

FOREIGN PATENT DOCUMENTS

| | | |
|---|---|---|
| WO | WO 96/30065 A1 | 10/1996 |
| WO | WO 97/10865 A1 | 3/1997 |
| WO | WO 1997/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 1999/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 A1 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/077384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 A1 | 11/2003 |
| WO | WO 03/097133 A1 | 11/2003 |
| WO | WO 03/099358 A2 | 12/2003 |
| WO | WO 04/007554 A1 | 1/2004 |
| WO | WO 04/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 | 10/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/044348 | 5/2005 |
| WO | WO 2005/056077 | 6/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/083115 | 7/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/059233 A1 | 5/2008 |
| WO | WO 2008/075033 A | 6/2008 |
| WO | WO 2008/093063 A2 | 8/2008 |
| WO | WO 2010/023303 A1 | 3/2010 |
| WO | WO 2010/056712 | 5/2010 |
| WO | WO 2011/117283 | 9/2011 |
| WO | WO-2011117283 A2 * | 9/2011 ............ A61M 5/326 |
| WO | WO 2012/000835 A1 | 1/2012 |
| WO | WO 2012/059517 | 5/2012 |
| WO | WO 2012/093071 | 7/2012 |
| WO | WO-2012117252 A1 * | 9/2012 .......... A61M 5/2033 |
| WO | WO 2012/140088 | 10/2012 |
| WO | WO 2012/155035 | 11/2012 |
| WO | WO 2013/070715 | 5/2013 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
International Search Report dated Sep. 5, 2005; International Application No. PCT/GB2005/002131.
International Search Report dated Sep. 9, 2005; International Application No. PCT/GB2005/002120.
International Search Report dated Sep. 5, 2005; International Application No. PCT/GB2005/002137.
International Search Report dated Sep. 6, 2005; International Application No. PCT/GB2005/002108.
International Search Report dated Sep. 5, 2005; International Application No. PCT/GB2005/002105.
International Search Report dated Sep. 5, 2005; International Application No. PCT/GB2005/002116.
International Search Report dated Sep. 5, 2005; International Application No. PCT/GB2005/002128.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.

(56) References Cited

OTHER PUBLICATIONS

International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Oct. 9, 2007; International Application No. PCT/GB2006/001023.
International Search Report dated Feb. 27, 2007; International Application No. PCT/IB2006/002792.
International Search Report dated Aug. 22, 2007; International Application No. PCT/GB2007/001992.
International Search Report dated Sep. 4, 2007; International Application No. PCT/GB2007/002002.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
International Search Report dated Oct. 14, 2008; International Application No. PCT/GB2008/002580.
International Search Report dated Nov. 27, 2008; International Application No. PCT/GB2008/002579.
International Search Report dated Oct. 10, 2008; International Application No. PCT/GB2008/002573.
International Search Report dated Oct. 10, 2008; International Application No. PCT/GB2008/002583.
International Search Report dated Sep. 30, 2009; International Application No. PCT/GB2009/001447.
International Search Report dated Oct. 2, 2009; International Application No. PCT/GB2009/001448.
International Search Report dated Oct. 5, 2009; International Application No. PCT/GB2009/001451.
International Search Report dated Oct. 6, 2009; International Application No. PCT/GB2009/001453.
International Search Report dated Oct. 5, 2009; International Application No. PCT/GB2009/001445.
International Search Report dated Jan. 22, 2010; International Application No. PCT/GB2009/001446.
International Search Report dated Jan. 12, 2008; International Application No. PCT/GB2008/002475.
International Search Report dated Sep. 4, 2003; International Application No. PCT/GB03/01946.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Jan. 29, 2015; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.
Page entitled 'Unusual cams' V. Ryan, 2002-2009; from www.technologystudent.com.
Cam Design and Manufacture; Preben W. Jensen; Industrial Press; New York; 1965; Chapter 1.
Definition of a cam taken from www.wikipedia.com, Feb. 7, 2012.
Farm gate latch image Website showing gate latches from Jun. 3, 2004, http://dictionary.cambridge.org/dictionary/british/latch.
Engineering Tolerance, definition, Aug. 15, 2013; http://en.wikipedia.org/wiki/Engineering_tolerance.
Witness statement statement by Mr. Jeremy Marshal, Head of Technology Development & CI of the opponent, Dec. 2, 2011.
Patient instruction leaflet Glaxo Mode d'emploi (FR); Referred to in Statement of Jeremy Marshall, Dec. 2, 2011.
Assembly instructions, process flow diagrams for AJ1200CE129 and AJ1200CA00 together with drawings for AJ501 all dated differently; starting in 1993 and the latest dates referring to 2002, Referred to in Statement of Jeremy Marshall, Dec. 2, 2011.
Discussion session at the 5th International Nurses' Workshop on Multiple Sclerosis.
Article from diabetes health, Feb. 1, 1997.
Parts list AJ503 Auto injector—Glaxo Jul. 29, 1992 (change 92-7-45)/ Oct. 18, 1993 with drawings dated between 1986 and 1991.
Photos of a sample, Referred to in Statement of Jeremy Marshall, Dec. 2, 2011.
Company's sales ledger for the period of Nov. 1991-May 1993.
510(k) pre-market notification Apr. 19, 1990.
Fax dated Jul. 21, 1995 Imigran injection launch data.
Patient instruction leaflet, Imigran, Referred to in Statement of Jeremy Marshall, Dec. 2, 2011.
Patient instruction leaflet Glaxo Neurologie (NL), Referred to in Statement of Jeremy Marshall, Dec. 2, 2011.
Parts list AJ501 stamped Aug. 6, 2002.
Patient instruction leaflet Imigran (EN), Referred to in Statement of Jeremy Marshall, Dec. 2, 2011.
Detailed view of the retainer component AJ613 dated Jun. 15, 1993 last amended Nov. 8, 1995.
Production drawing Nov. 18, 2003, Autoject2 fixed needle AJ-0530-00-00-33.
Bill of material amendments log, Dec. 2, 2011.
Internet archive pages dated Dec. 4, 1999_1.
Internet archive pages dated Dec. 4, 1999_2.
Invoices of sales Dec. 12, 2005 Autoject 2—Product code AJ1300EA000 and invoice of sales Mar. 21, 2006 Autoject 2—Product code AJ1311EA000.
Hospital price list Mar. 1990 and pharmacy trade price list Mar. 1994 losing an Autoinjector AJ1200.
Production record of Feb. 15, 2001 referring to device part AJ501 and a packaged part No. AJ1200CA00, dated Feb. 15, 2001.
Production record, dated raised Feb. 15, 2001.
Parts list for AJ501, Referred to in Statement of Jeremy Marshall, Dec. 2, 2011.
General assembly drawing issued May 2, 1986, last amended Feb. 9, 1994.
Extracts from the company's sales ledger, Referred to in Statement of Jeremy Marshall, Dec. 2, 2011.
Extract from a medical shop catalogue, Referred to in Statement of Jeremy Marshall, Dec. 2, 2011.
Mechanical Engineer's Handbook; Dan B. Marghitu, J. David Irwin; Academic Press, Burlington, 2001.
Non-patent literature ISO 11040-4:1996('E').
European Pharmacopeia, 2002, p. 282-283.
"Starlock Fasteners": filed at the EPO by way of the opponent's letter of Apr. 3, 2013 and said to be retrieved from the website www.bakfin.com around that time.
Worksheet referred to in document A21; V. Ryan, 2002-2009; from www.technology student.com.
Dictionary definition of a latch; http://dictionary.cambridge.org/dictionary/bristish/latch, Oct. 12, 2014.
"Farm Gate Latch Image": filed at the EPO by way of the opponent's letter of Oct. 31, 2014.
GA drawing dated Jun. 10, 1994 several times amended.
Article Apr. 27, 2002 5th International Nurses' Workshop on Multiple Sclerosis.

* cited by examiner

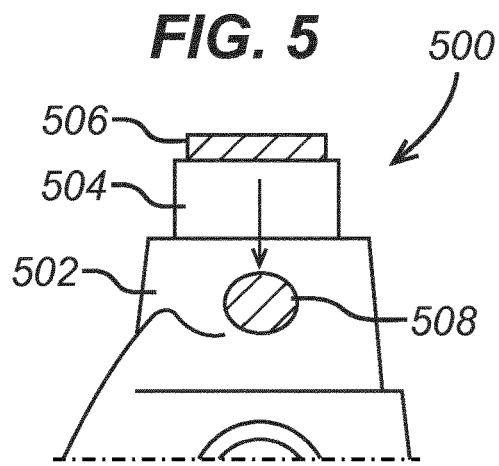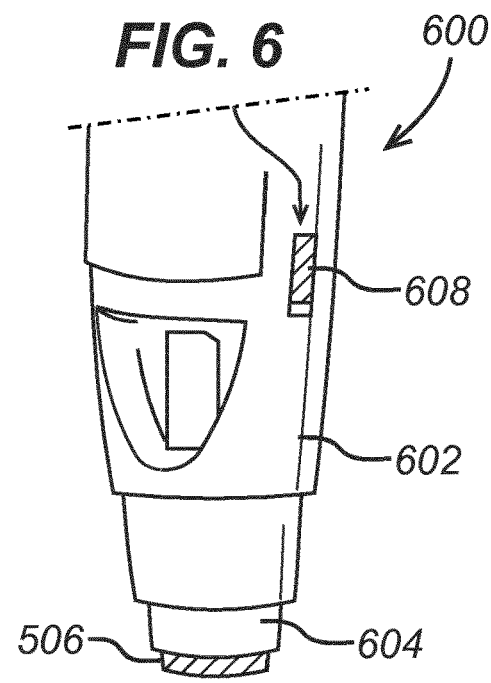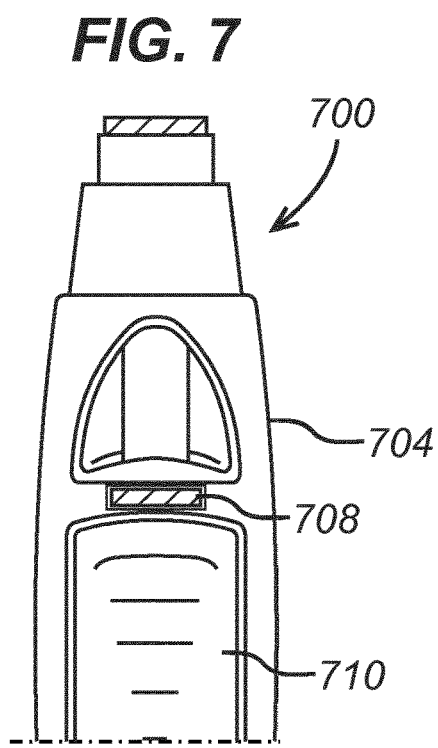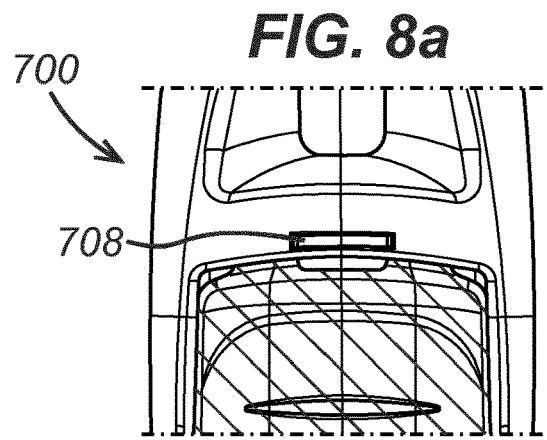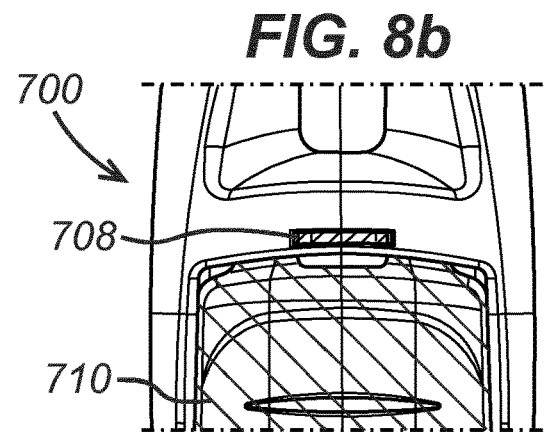

INJECTION DEVICE

FIELD OF THE INVENTION

The present invention relates to an injection device for delivering an injection, as well as an injection kit and a method of operating the injection device.

BACKGROUND OF THE INVENTION

Auto-injectors are known from WO 95/35126 and EP-A-0 516 473 and tend to employ a drive spring and some form of release mechanism that releases the syringe from the influence of the drive spring once its contents are supposed to have been discharged, to allow it to be retracted by a return spring.

An auto-injector is known from WO 2007/036676 which has a locking mechanism which must be disengaged before the release mechanism can be activated. In its locked position, the locking mechanism also prevents forward movement of the syringe out of the injection device against the bias of the return spring, for example when a cap gripping a boot covering the syringe needle, is removed. In the injection device described in WO 2007/036676, the locking mechanism comprises a sleeve which protrudes from an open end of the injection device. The sleeve is biased into its extended position by a resilient spring mechanism which must be overcome to disengage the locking mechanism. The locking mechanism can be disengaged by, for example, moving the sliding sleeve inwardly into the injection device (i.e. retracting the sleeve). This can be done by forcing the end of the sliding sleeve against tissue and then activating the release mechanism.

It has been found that users of injection devices, such as those described in WO2007/036676, struggle to discern when the sliding sleeve has been retracted sufficiently order to allow activation of the device. This can be very frustrating for users, since they may make numerous unsuccessful attempts at activating the injection since they are unaware that the sliding sleeve has not been fully retracted. Further, the frustrated user may attempt to force the injection device, i.e. by applying excessive pressure to the trigger, and so damage the injection mechanism.

There is therefore a need to provide an injection device that informs the user as to the progress of the injection device from a locked state to a state in which the injection may be carried out. The present invention addresses such a problem.

SUMMARY OF THE INVENTION

A first aspect of the present invention provides an injection device comprising an actuator adapted when actuated to cause commencement of an injection sequence; a locking mechanism adapted to be moved between a locked position in which the locking mechanism prevents the actuator from being actuated, and an unlocked position in which the actuator can be actuated to cause commencement of the injection sequence; and an indicator configured to provide a visual indication of whether the locking mechanism is in its locked position or in its unlocked position.

The indicator permits a user to visually inspect the status of the locking mechanism and thereby discern whether or not the actuator may be actuated. Thus, the user need no longer hope or presume that the locking mechanism is in its unlocked state after attempting to move it there, but instead may obtain visual confirmation of that fact, or else see that more effort is required before actuating the actuator. This has been found to be comforting to users, particularly those with poor dexterity who may struggle to operate an injection device with such safely features.

The indicator may comprise an indicator component on the indicator which moves with the locking mechanism as it moves between its locked and unlocked positions. In an implementation which is straightforward to manufacture, the indicator may form part of the same component as the locking mechanism. Thus, no additional components are required. Moreover, the probability of the indicator functioning correctly (i.e. wherein the indication as to whether the locking mechanism is in an unlocked state is correct) is maximised, since it is not subject to external tolerances, and instead relates directly to the progress of the locking mechanism. Alternatively, the injection device may comprise a separate sliding component which forms the indicator, and which is acted on by the locking mechanism, either directly or via one or more additional components. This is advantageous because the separate sliding component may be specifically designed to maximise visibility of that component, and is therefore not subject to the design constraints of the locking mechanism.

The injection device may further comprise a housing to which the actuator and locking mechanism are moveably mounted. The housing may comprise an indicator aperture to facilitate visual inspection of the indicator. This permits the components of the indicator to be housed internally to the injection device, which protects them against tampering or damage.

Preferably at least part or all of the indicator component is visible through the indicator aperture when the locking mechanism is in its locked position. On the one hand, the aperture may be very large, such that a substantial portion of the locking mechanism is visible, and the indicator may be a simple mark on the locking mechanism, the progress of which may be monitored through the aperture by the user. In that case, the user may see that the injection device is able to be actuated when the mark aligns with another mark on the housing, for instance. On the other hand, the aperture may be relatively small, and the indicator may simply be a particular portion of the locking mechanism itself, for instance a particular portion of having a distinct colour which is different from the remainder of the mechanism. In that case, the user may see that the injection device is able to be actuated when the aperture is entirely full of the distinct colour.

Of course, it will be appreciated that a coloured portion is just one way of providing a visual indicator in the present invention. The indication may be provided by one or more sections of different colour corresponding to the different states; by a colour gradient (for example red transitioning to green); by one or more symbols, characters or images on the indicator corresponding to the different states; or any other way which would occur to a skilled person.

The relationship between the indicator and the indicator aperture may be implemented in various ways, as described below.

The indicator aperture may be wholly covered by at least a part of the indicator component when the locking mechanism is in its locked position. At least part of the indicator aperture may be not covered by the indicator component when the locking mechanism is not in its locked position.

Moreover, at least part or all of the indicator component may be visible through the indicator aperture when the locking mechanism is in its unlocked position.

Alternatively, the indicator aperture may be wholly covered by at least a part of the indicator component when the locking mechanism is in its unlocked position. At least part of the indicator aperture may be not covered by the indicator component when the locking mechanism is not in its unlocked position.

The locking mechanism may comprise a contact portion which is adapted to contact an engagement surface of the actuator when the locking mechanism is in its locked position. Thus, a physical barrier is provided against the actuator, which prevents the actuator from being actuated accidentally when the locking mechanism is in its locked position. The contact portion may be adapted not to contact an engagement surface of the actuator when the locking mechanism is in its unlocked position. For example, the physical barrier may be completely removed from interfering with the actuator when the locking mechanism is in its unlocked position.

In a particularly preferred embodiment, the locking mechanism is moveable between its locked position and its unlocked position such that the contact portion moves from a position in which it contacts the engagement surface of the actuator to a position in which it no longer contacts the engagement surface of the actuator.

The actuator may be configured to move between a first position in which commencement of the injection sequence is prevented, and a second position in which commencement of the injection sequence occurs. The actuator may rotate between its first and second positions about a pivot.

In certain embodiments of the invention, the injection device further comprises a drive mechanism. In such embodiments, the actuator may comprise a locking surface which inhibits the drive mechanism when the actuator is in its first position and which does not inhibit the drive mechanism when the drive mechanism is in its second position.

Preferably, the injection device further comprises a syringe which is moveable by the drive mechanism on commencement of the injection sequence from a position in which the syringe is wholly contained within a body of the injection device to a position in which a needle of the syringe extends from a housing of the injection device via an injection opening, wherein the drive mechanism is adapted to expel contents of the syringe via the needle when the syringe is in its extended position. Naturally a syringe is merely preferred, and other means for containing and ejecting medicaments may be provided, such as vials or ampules with or without integral needles or cannula.

Preferably, the locking mechanism comprises a sliding component which slides to move the locking mechanism between its locked and unlocked positions. The sliding component may be configured to slide inwardly into the injection device to move it from its locked position to its unlocked position.

The sliding component may project from a sliding component opening (typically, but not necessarily, the injection opening) in the housing when it is in its unlocked position. Thus, the sliding component may engage the skin of a user, and be moved inwardly into the housing of the injection device as the user pushes the injection device towards the skin. In a preferred embodiment, the sliding component is a sliding sleeve.

In any embodiment, the injection device may contain a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

By 'the injection device may contain a substance' it is meant that the substance may be contained within a suitable medicament container, such as a vial or syringe, within the injection device. Such medicament container may contain other substances, such as further active or inactive ingredients.

In a further aspect of the invention, a substance is provided, the substance being selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of said substance to a human subject using an injection device according to any of the above embodiments.

In yet another aspect of the invention, an injection device is provided for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, to a human subject by using the injection device, where the injection device is an injection device of any of the above embodiments.

By 'delivery of a substance' it is meant that the injection device is used to inject said substance into the human subject, for example by subcutaneous, intradermal or intramuscular injection. Said substance may be administered in combination with other substances, such as further active or inactive ingredients.

BRIEF DESCRIPTION OF THE DRAWINGS

The present invention is now described by way of example with reference to the accompanying drawings, in which:

FIG. 5 depicts a first embodiment of an injection device of the present invention;

FIG. 6 depicts a second embodiment of an injection device of the present invention;

FIG. 7 depicts a third embodiment of an injection device of the present invention;

FIGS. 8a and 8b depict the indicator of the embodiment in FIG. 7 in the locked and unlocked positions more detail;

DETAILED DESCRIPTION OF THE DRAWINGS

Figure 1:
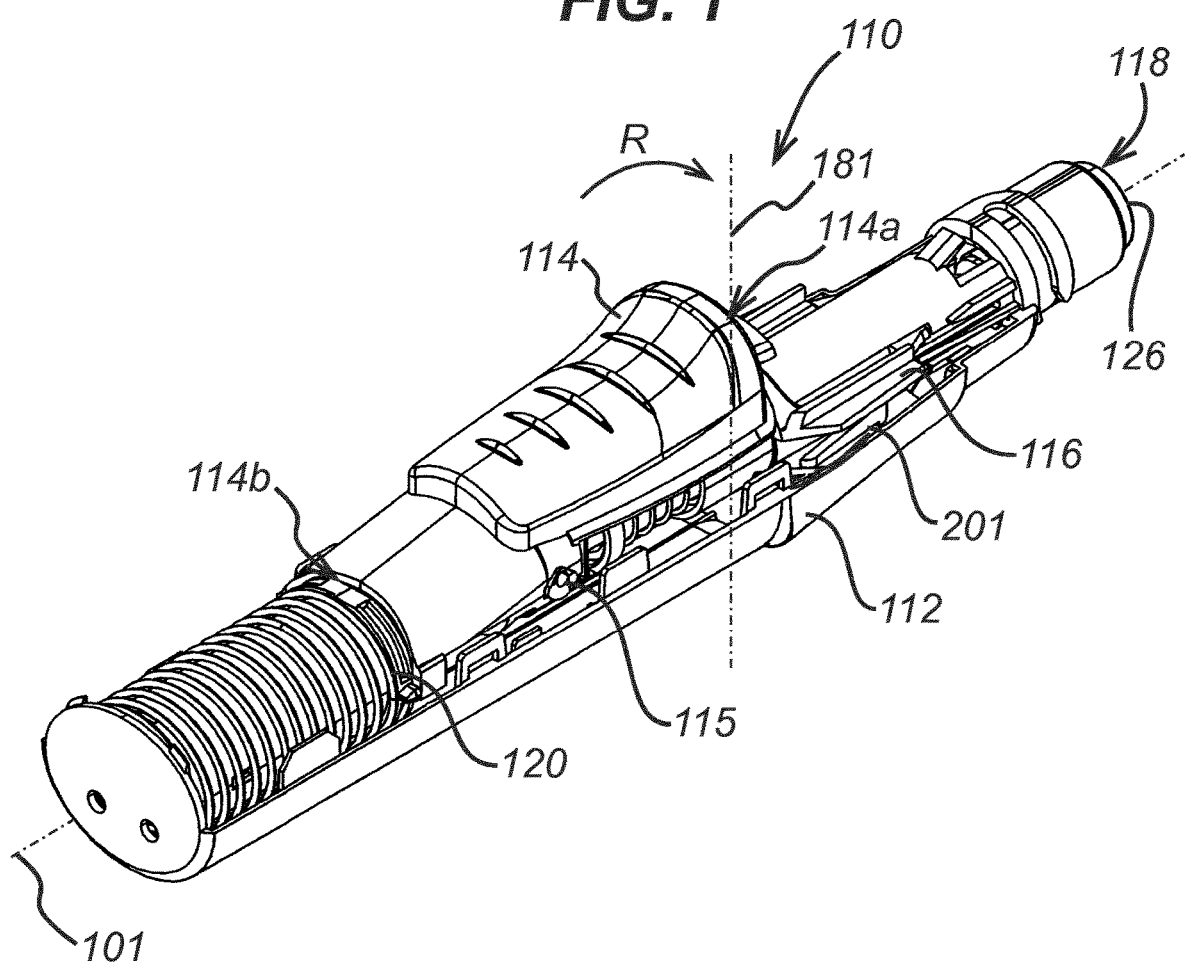
FIG. 1 depicts an exemplary injection device showing the mechanism within the housing.
Figure 2:
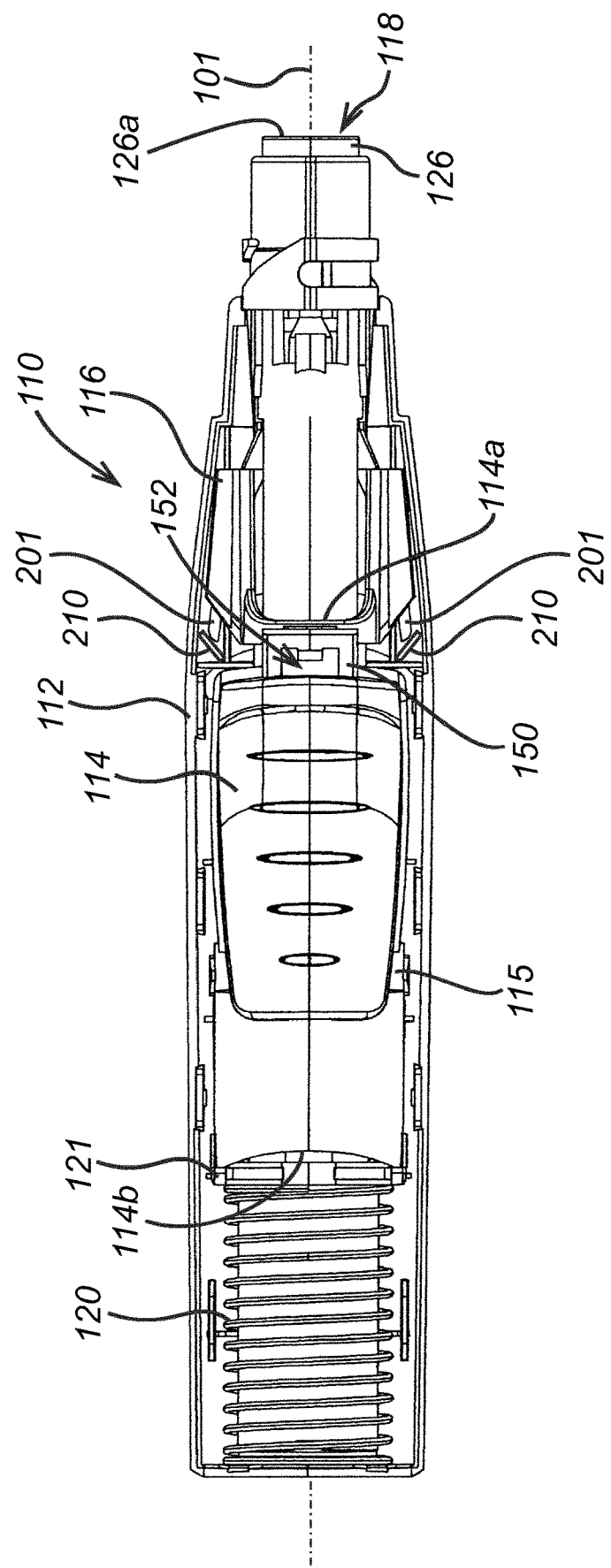
FIG. 2 depicts a plan view of an injection device of the present invention.

An exemplary injection device 110 is depicted in FIGS. 1 and 2. The injection device 110 has an injection device housing 112 and a longitudinal axis 101. FIGS. 1 and 2 depict only the lower half of the housing 112. The upper part of housing 112 is absent so that the internal mechanism can be clearly seen.

A syringe (not shown) is contained in the housing 112. The injection device 110 comprises a trigger 114 as part of the activation means. The trigger 114 is rotatable about a pivot 115 from a rest position (as shown in FIG. 2) to an active position. The proximal end 114b of the trigger 114 connects with a drive coupling 121 which is acted upon by a drive spring 120. The drive coupling 121 is in communication with the syringe. The drive coupling and drive spring all form part of the activation means which allow the delivery of the injection by acting on the syringe.

The injection device 110 comprises a release mechanism 126 in the form of a cylindrical sleeve that protrudes from the distal end of the injection device 110.

In order to effect delivery of the injection, the trigger 114 is rotated about the pivot 115 in a direction R (i.e. downwards into the housing 112 at its first end 114a). This causes the second end 114b of the trigger 114 to disengage from the drive coupling 121, thereby letting the drive spring 120 drive the syringe 122 (via the drive coupling 121) along the longitudinal axis 101 and out of an aperture 118 in the housing 112.

Figure 3:
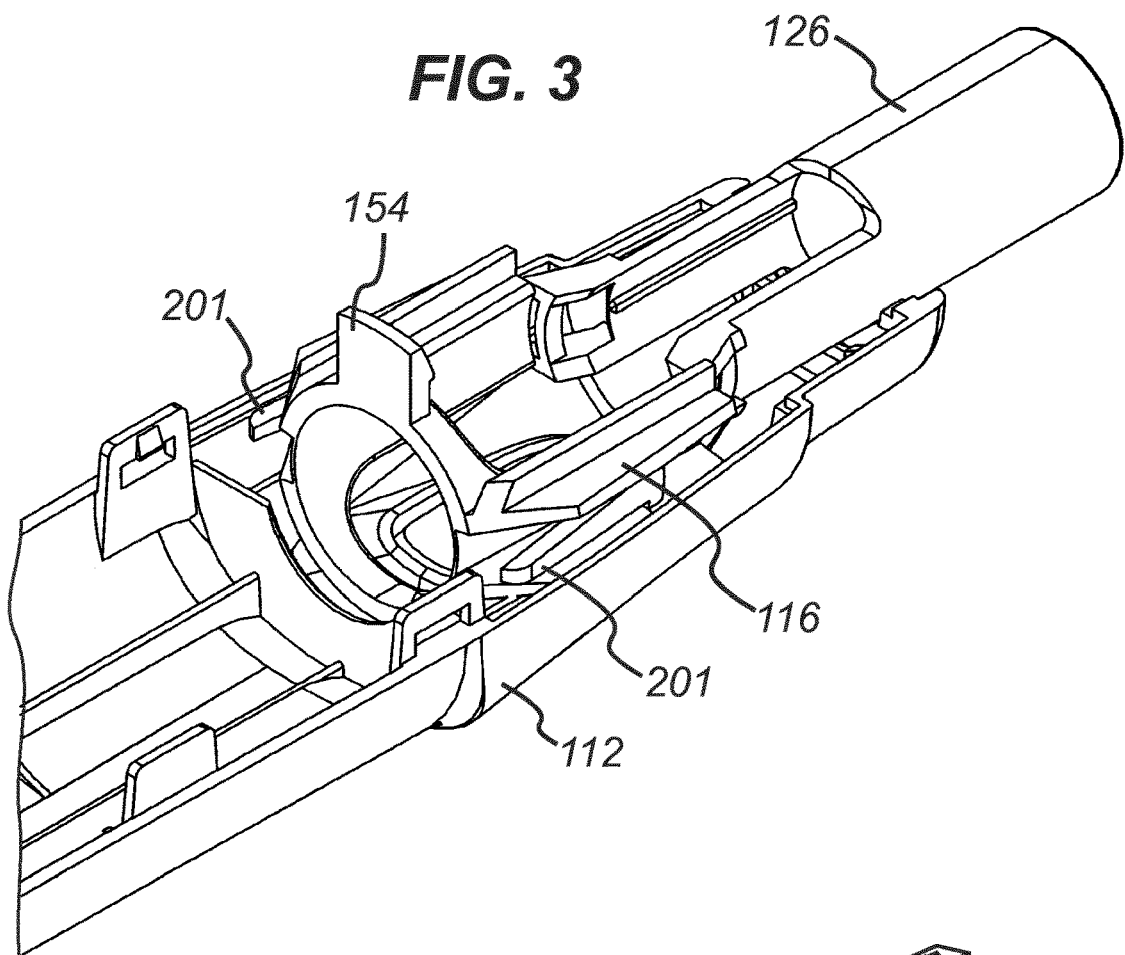
FIG. 3 depicts the detail of the release mechanism of an injection device of the present invention.
Figure 4:
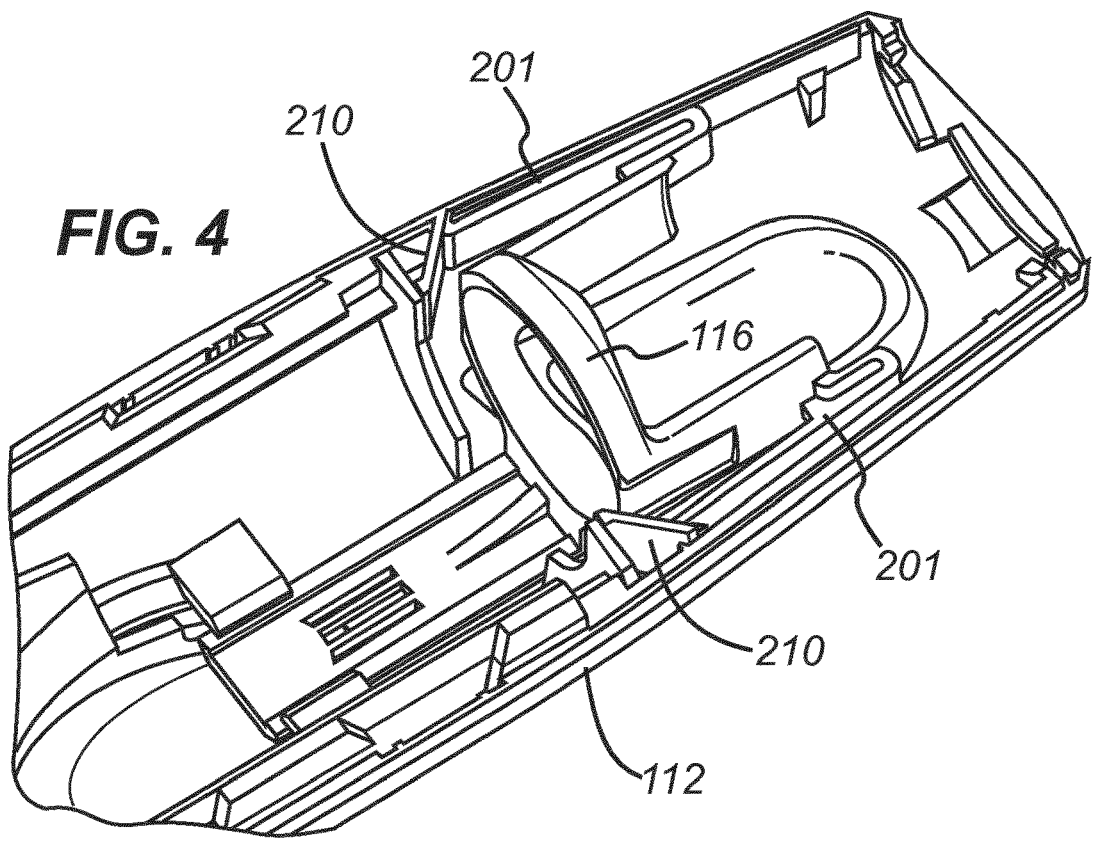
FIG. 4 depicts a detailed view of parts of the release mechanism of an injection device with the present invention.

However, when the release mechanism 126 is in its impeding position, which corresponds to the release mechanism protruding from the distal end of housing 112, an impediment in the form of a protrusion 154 (as depicted in FIG. 3) is positioned so as to abut the under-surface of portion 150 of trigger 114. In this way, the protrusion 154 impedes the rotation of the trigger and thus impedes the delivery of the injection. In order to carry out the injection, the release mechanism is moved into a second position, which corresponds to the release mechanism 126 being moved into the housing 112 along the direction of the longitudinal axis 101. When the release mechanism is in its second position the protrusion 154 aligns with cut out 152 in trigger 114. Protrusion 154 can be received in cut out 152 and so the trigger can be rotated about pivot 115 and the delivery of the injection can be effected.

The release mechanism comprises a frame 116 extending proximally from a sliding sleeve 126. The protrusion 154 extends radially outwardly from a proximal portion of the frame 116. The frame is configured to couple the sliding sleeve portion 126, which engages the skin of a user at the distal-most end of the device, to the protrusion. It does so with two proximally extending legs, thereby using as little excess material as possible to prevent wastage and to avoid interference with other components of the injection device. Thus, the frame is largely open.

Turning now to FIG. 5, a first embodiment of an injection device 500 according to the invention is shown. As with the exemplary injection device described above, the injection device 500 comprises a housing 502 having a casenose 504 and a sliding sleeve 506 configured to engage the skin of a user and thus be pushed proximally within the housing 502 of the device. As described above, the sliding sleeve is movable from a locked position, in which it prevents an actuator (such as a trigger) from being activated, to an unlocked position, in which it does not.

The casenose of the housing comprises an aperture 508 through which a user may look to visually inspect the locking mechanism—in this case, the sliding sleeve 506 portion. The aperture may be a hole, or may be a transparent or translucent material. Through the aperture 508, the sliding sleeve is visible. The sliding sleeve thus acts as an indicator to the user as to the status of the sliding sleeve. For example, when the sliding sleeve is in a locked position, the indicator will show one scenario and when the sliding sleeve is in an unlocked position, the indicator will show another scenario. This is described in more detail below.

A second embodiment of an injection device 600 according to the invention is shown in FIG. 6. Like reference numerals depict corresponding features vis-à-vis FIG. 5. Again, the housing 604 comprises an aperture 608 through which a user may look to visually inspect the locking mechanism. However, with this embodiment the aperture is located not in the casenose 604, but in the main body of the housing 602. The aperture 608 is radially offset with respect to the actuator (i.e. trigger), such that it easily to see when the injection device is held in the preferred fashion.

A third embodiment of an injection device 700 according to the invention is shown in FIG. 7. Like reference numerals depict corresponding features vis-à-vis FIGS. 5 and 6. Again, the housing 704 comprises an aperture 708 through which a user may look to visually inspect the locking mechanism. However, with this embodiment the aperture is located in the main body of the housing 702, but radially aligned with respect to the actuator (i.e. trigger) 710. Locating the aperture 708 at this part of the housing makes it easy to see when the injection device is held in an alternative fashion, and also permits a convenient internal arrangement of components, as described in more detail below.

FIGS. 8a, 8b, 9 and 10 show the third embodiment of the invention in use. In particular, FIG. 8a shows the visual indicator through the aperture 708 when the locking mechanism is in the locked position. FIG. 8b shows the visual indicator through the aperture 708 when the locking mechanism is in the unlocked position. As can be seen, the appearance of the visual indicator has changed, indicating that the locking mechanism is in the unlocked position.

Figure 9:
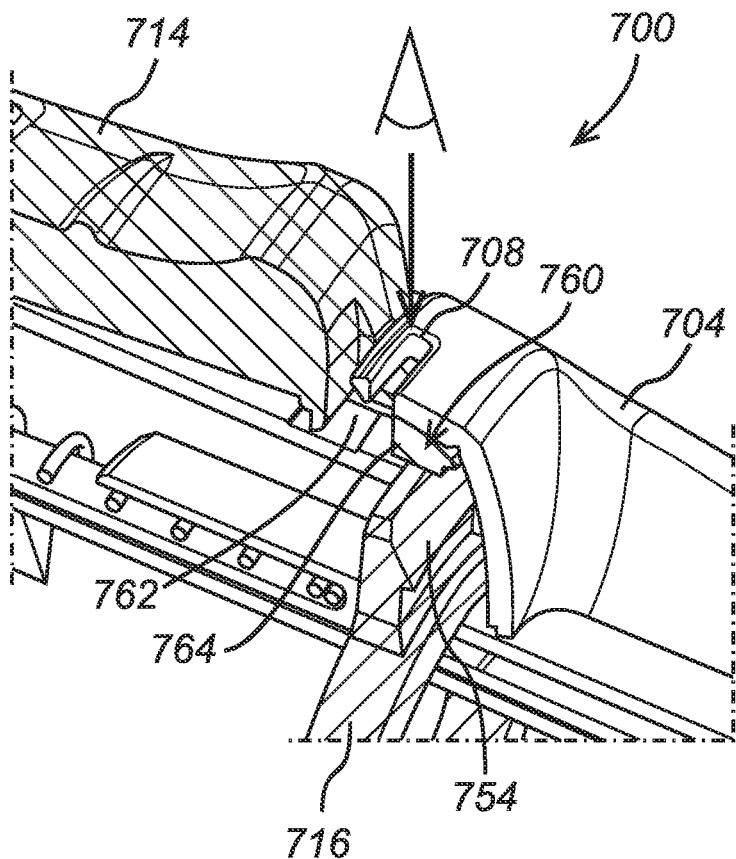
FIG. 9 depicts the internal mechanism of the embodiment of FIG. 7 in more detail.

FIG. 9 shows the internal mechanisms of the embodiment of FIG. 7 in more detail. Here, it can be seen that locking mechanism provides a frame 716 from which protrusion 754 extends. As described above with respect to FIGS. 1 to 4, the protrusion engages the actuator (i.e. trigger 714) in the locked position thereby preventing the actuator from being actuated. In more detail, the actuator 714 comprises an extension portion 760 which extends distally from the distal end of the trigger 714. The extension portion comprises a cut out 762 and a tab 764. In the locked position, the extension portion 760 engages the tab 764. In the unlocked position, the extension portion 760 engages the cut out 762.

It can also be seen that the aperture 708, which is radially aligned with the actuator, is located in the region of the extension portion 760, and directly over the cut out 762. Hence, when the locking mechanism is in the locked position, the locking mechanism (specifically, the extension portion) is not visible since it engages the tab. However, when the locking mechanism is in the unlocked position and engages the cut out, the locking mechanism (specifically, the extension portion) is visible through the aperture. Thus, a portion of locking mechanism itself acts a visual indicator of the status of the locking mechanism. By making the locking mechanism (specifically, the extension portion) a distinctive colour, the visual indicator is even more effective.

Figure 10:
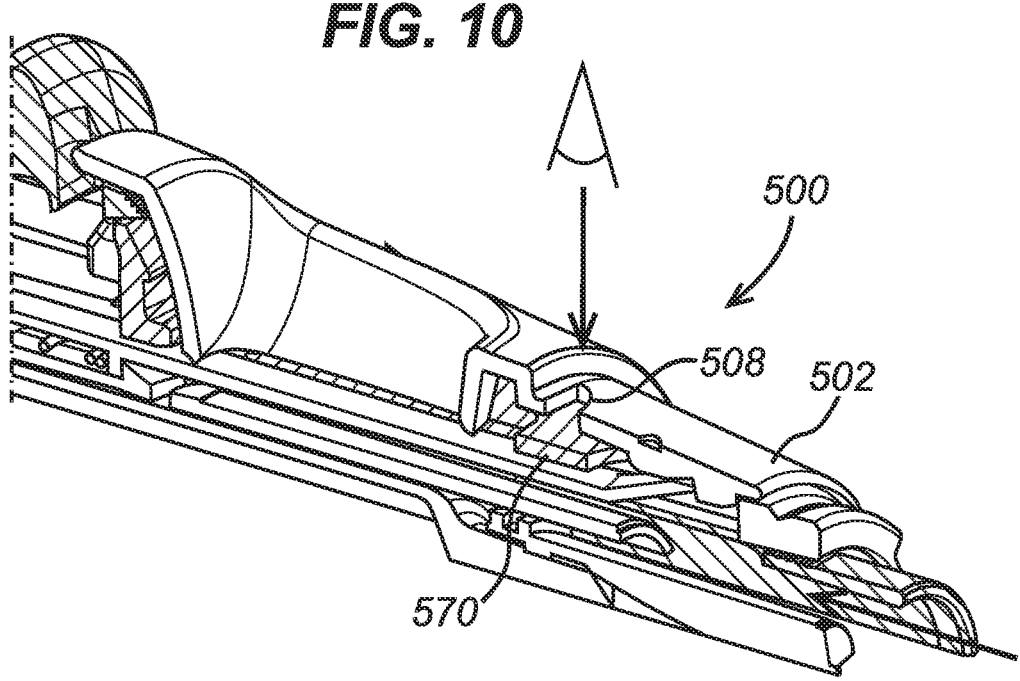
FIG. 10 depicts the internal mechanism of the embodiment of FIG. 5 in more detail.

FIG. 10 shows the internal mechanisms of the embodiment of FIG. 5 in more detail. The locking mechanism and actuator is identical to that shown in FIG. 9, except for the addition of an extra indicator tab 570, discussed in more detail below.

The aperture 508 is located in the casenose portion of the housing; that is, not in the region of the extension portion 560. Accordingly, an indicator tab 570 is provided on the locking mechanism in the region of the casenose. When the locking mechanism is in the locked position, the locking mechanism (specifically, the indicator tab 570) is not visible since it is not in line with the aperture 508. However, when the locking mechanism is in the unlocked position the locking mechanism (specifically, the indicator tab 570) moves into line with the aperture 508 and is thus visible through the aperture. Thus, again, a portion of locking mechanism itself acts a visual indicator of the status of the locking mechanism. Again, by making the locking mechanism (specifically, the extension portion) a distinctive colour, the visual indicator is even more effective.

Figure 11:
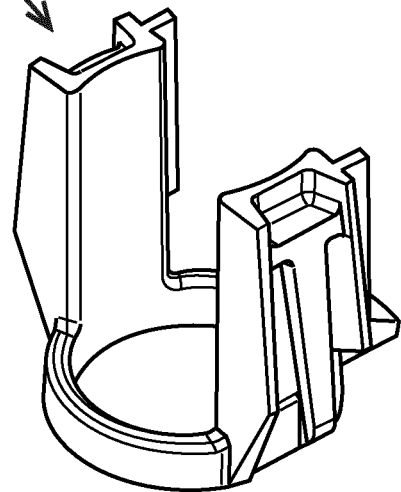
FIG. 11 depicts a frame element of an exemplary injection device.
Figure 12:
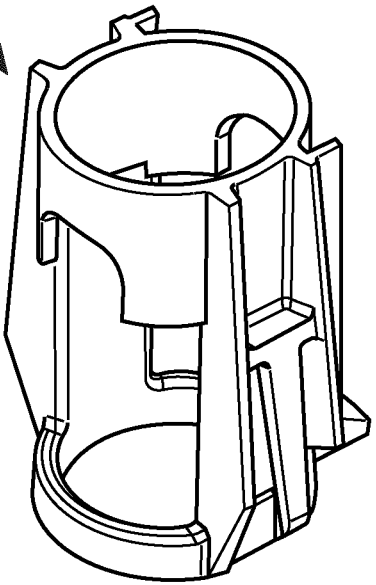
FIG. 12 depicts a frame element of the embodiment of FIG. 10.

FIG. 11 shows a frame element 1116 used in an exemplary injection device. FIG. 12 shows a frame element 1216 used in the injection device of FIG. 10. As can be seen, the frame element 1216 comprises an indicator tab 516 at its distal end. The indicator tab 516 comprises an annular band of material with a cut out therein.

Figure 13:
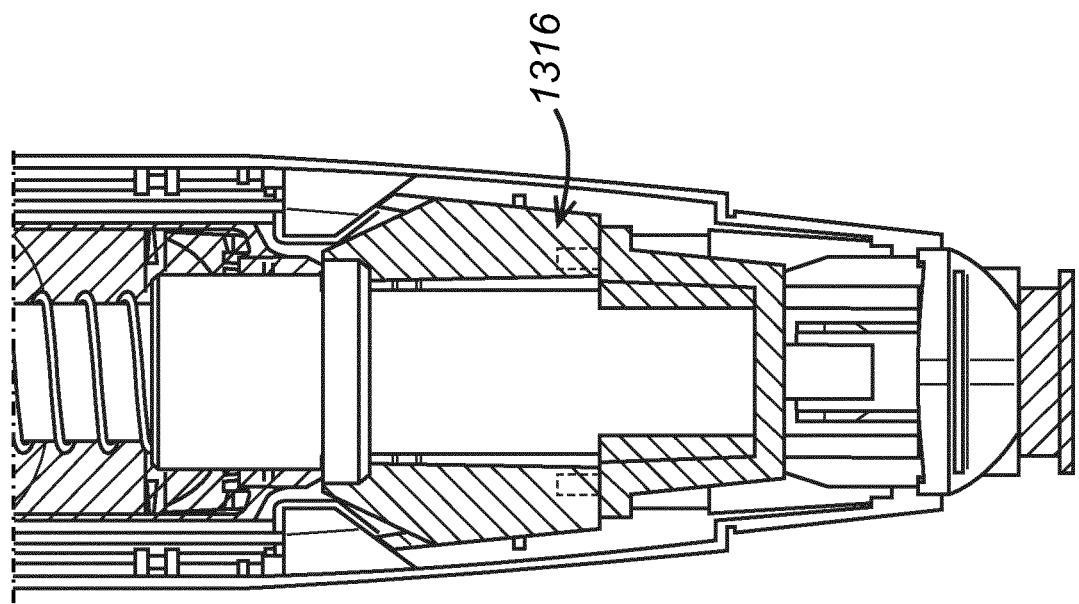
FIGS. 13 to 15 depict an alternative embodiment to that shown in FIG. 10.
Figure 14:
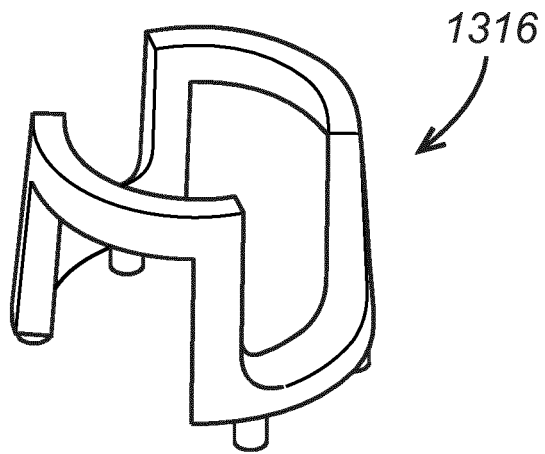
Figure 15A:
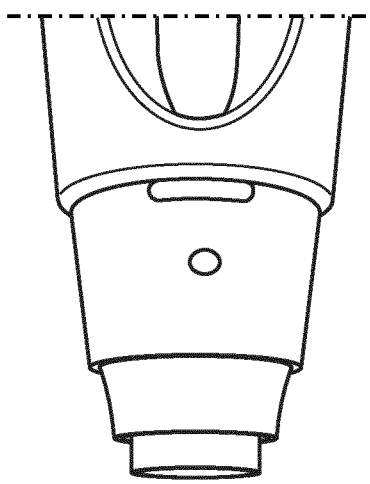
Figure 15B:
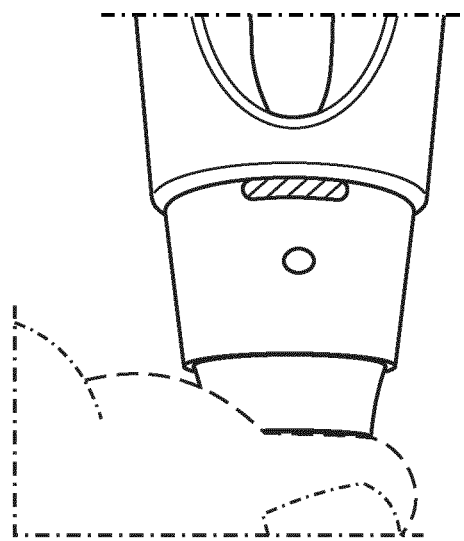

FIGS. 13 and 14 show an alternative frame element 1316 usable with an aperture in the casenose portion of an injection device. FIGS. 15a and 15b show the alternative frame element in use, wherein it can be moved into and out of alignment with an aperture in the case nose.

The skilled person would appreciate that the above embodiments could be implemented the other way around; that is, the locking mechanism could be configured to be in line with the aperture when it is in the locked position and moved out of line with the aperture when in the unlocked position. Depending on the particular location of the aperture and the particular configuration of the frame element, extension portion or indicator tab, the device may indicate to the user that the locking mechanism is in the locked position when the indicator aperture is wholly covered by at least a part of the indicator component and that the locking mechanism is not in its locked position when at least part of the indicator aperture is not covered by the indicator component. Alternatively the device may indicate to the user that the locking mechanism is in the unlocked position when the indicator aperture is wholly covered by at least a part of the indicator component and that the locking mechanism is not in its unlocked position when at least part of the indicator aperture is not covered by the indicator component.

The skilled person would furthermore appreciate that the locking mechanism could be provided as a single integrally molded component, or as separate components. For instance the frame elements could be separate from, and mechanically coupled to the sliding sleeve, or else could be provided as a single integrated component.

In use, such an injection device as described above might be used to deliver substances such as:

golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity. In addition to these substances, any medicament contained within the injection device may also include other substances, such as inactive ingredients, as a skilled person would appreciate.

It will of course be understood by the person skilled in the art that particular substances are efficacious for use in the treatment or prevention of particular conditions, as is well known in the art. For instance, it is known that antiallergics are efficacious for use in the treatment or prevention of allergies; antihistamines are efficacious for use in the treatment or prevention of hay fever; anti-inflammatories are efficacious for use in the treatment or prevention of inflammation; and so on. Accordingly, any selection of one or more substances listed herein or in the claims for use in the treatment or prevention of one or more conditions for which those substance(s) are known to be efficacious is envisaged.

In a particular example, however, golimumab is known to be efficacious for use in the treatment or prevention of one or more of rheumatoid arthritis, psoriatic arthritis, ankylosing spondylitis or ulcerative colitis, or any combination of rheumatoid arthritis, psoriatic arthritis, ankylosing spondylitis and ulcerative colitis, or all of rheumatoid arthritis, psoriatic arthritis, ankylosing spondylitis and ulcerative colitis.

Golimumab may optionally be used in combination with one or more inactive ingredients such as any or all of L-histidine, L-histidine monohydrochloride monohydrate, sorbitol, polysorbate 80, and water. Golimumab may present in a composition in which golimumab is the only active ingredient. For example, golimumab may administered as SIMPONI®.

It will of course be understood that the present invention has been described above purely by way of example and modifications of detail can be made within the scope of the invention.

The invention claimed is:

1. An injection device comprising:
a housing comprising an indicator aperture, the housing defining a longitudinal axis;
a trigger movable between a first position and a second position to commence an injection, wherein commencement of an injection sequence is prevented when the trigger is in the first position;
a locking mechanism comprising a sliding component having a skin-engaging surface, the sliding component slidable along the longitudinal axis with respect to the housing between a locked position in which the locking mechanism prevents the trigger from being moved from the first position to the second position and an unlocked position in which the trigger is movable from the first position to the second position to commence the injection;
an indicator movable with the locking mechanism along the longitudinal axis with respect to the housing, wherein the indicator is housed internally to the injection device and viewable through the indicator aperture to provide a visual indication of whether the locking mechanism is in the locked position or in the unlocked position;
a drive mechanism, wherein the trigger comprises a locking surface which inhibits the drive mechanism when the trigger is in the first position and which does not inhibit the drive mechanism when the trigger is in the second position; and
a syringe which is moveable by the drive mechanism upon movement of the trigger to the second position, from a position in which the syringe is wholly contained within a body of the injection device to an extended position in which a needle of the syringe extends from the housing via an injection opening, wherein the drive mechanism is adapted to expel contents of the syringe via the needle when the syringe is in the extended position.

2. The injection device of claim 1, wherein the indicator comprises an indicator component on the indicator which moves with the locking mechanism as the locking mechanism moves between the locked position and the unlocked position.

3. The injection device of claim 2, wherein at least part or all of the indicator component is visible through the indicator aperture when the locking mechanism is in the locked position.

4. The injection device of claim 3, wherein the indicator aperture is wholly covered by at least a part of the indicator component when the locking mechanism is in the locked position, and at least part of the indicator aperture is not covered by the indicator component when the locking mechanism is not in the locked position.

5. The injection device of claim 3, wherein the indicator aperture is wholly covered by at least a part of the indicator component when the locking mechanism is in the unlocked position, and at least part of the indicator aperture is not covered by the indicator component when the locking mechanism is not in the unlocked position.

6. The injection device of claim 2, wherein at least part or all of the indicator component is visible through the indicator aperture when the locking mechanism is in the unlocked position.

7. The injection device of claim 1, wherein the locking mechanism comprises a contact portion adapted not to contact an engagement surface of the trigger when the locking mechanism is in the unlocked position.

8. The injection device of claim 1, wherein the sliding component is a sliding sleeve.

9. The injection device of claim 1, wherein the trigger rotates between the first position and the second position about a pivot.

10. An injection device comprising:
a housing comprising an indicator aperture, the housing defining a longitudinal axis;
a trigger movable between a first position and a second position to commence an injection, wherein commencement of an injection sequence is prevented when the trigger is in the first position;
a locking mechanism comprising a sliding component having a skin-engaging surface, the sliding component slidable along the longitudinal axis with respect to the housing between a locked position in which the locking mechanism prevents the trigger from being moved from the first position to the second position and an unlocked position in which the trigger is movable from the first position to the second position to commence the injection;
an indicator movable with the locking mechanism and viewable through the indicator aperture to provide a visual indication of whether the locking mechanism is in the locked position or in the unlocked position;
a drive mechanism, wherein the trigger comprises a locking surface which inhibits the drive mechanism when the trigger is in the first position and which does not inhibit the drive mechanism when the trigger is in the second position; and
a syringe which is moveable by the drive mechanism upon movement of the trigger to the second position, from a position in which the syringe is wholly contained within a body of the injection device to an extended position in which a needle of the syringe extends from the housing via an injection opening, wherein the drive mechanism is adapted to expel contents of the syringe via the needle when the syringe is in the extended position;
wherein the locking mechanism comprises a contact portion adapted to contact an engagement surface of the trigger when the locking mechanism is in the locked position.

11. The injection device of claim 10 or claim 7, wherein the locking mechanism is moveable between the locked position and the unlocked position such that the contact portion moves from a position in which the contact portion contacts the engagement surface of the trigger to a position in which the contact portion no longer contacts the engagement surface of the trigger.

12. The injection device of any one of claims 1, 2, and 3 to 10, wherein the sliding component slides to move the locking mechanism between the locked position and the unlocked position.

13. The injection device of claim 12, wherein the sliding component is configured to slide inwardly into the injection device to move the locking mechanism from the locked position to the unlocked position.

14. The injection device of claim 13, wherein the sliding component projects from a sliding component opening in the housing when the locking mechanism is in the unlocked position.

15. An injection device according to any one of claims 1, 2, and 3 to 7, containing a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

16. An injection device for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, to a human subject by using the injection device, wherein the injection device is an injection device according to any one of claims 1, 2 and 3 to 7.

17. An injection device comprising:
a housing comprising an indicator aperture, the housing defining a longitudinal axis;
a trigger movable between a first position and a second position to commence an injection;
a locking mechanism comprising a sliding component having a skin-engaging surface, the sliding component slidable along the longitudinal axis with respect to the housing between a locked position in which the locking mechanism prevents the trigger from being moved from the first position to the second position and an unlocked position in which the trigger is movable from the first position to the second position to commence the injection;
an indicator movable with the locking mechanism along the longitudinal axis with respect to the housing, wherein the indicator is housed internally to the injection device and viewable through the indicator aperture to provide a visual indication of whether the locking mechanism is in the locked position or in the unlocked position;
a drive mechanism, wherein the trigger comprises a locking surface which inhibits the drive mechanism when the trigger is in the first position and which does not inhibit the drive mechanism when the drive mechanism is in the second position; and
a syringe which is moveable by the drive mechanism from a position in which the syringe is wholly contained within the housing of the injection device to a position in which a needle of the syringe extends from the housing of the injection device via an injection opening, wherein the drive mechanism is adapted to expel contents of the syringe via the needle when the syringe is in an extended position, wherein the locking mechanism comprises the sliding component which slides to move the locking mechanism between the locked position and the unlocked position, wherein the sliding component is configured to slide inwardly into the injection device to move the locking mechanism from the locked position to the unlocked position, wherein the sliding component projects from a sliding component opening in the housing when the locking mechanism is in the unlocked position, and wherein the sliding component opening is the injection opening.

* * * * *